United States Patent [19]
Yamamoto et al.

[11] 3,994,587
[45] Nov. 30, 1976

[54] DENSITOMETER

[75] Inventors: Hiroshi Yamamoto; Takashi Kurita; Jugoro Suzuki; Rikuo Hira; Hideki Makabe, all of Kyoto, Japan

[73] Assignee: Shimadzu Seisakusho Ltd., Kyoto, Japan

[22] Filed: July 22, 1975

[21] Appl. No.: 598,005

[30] Foreign Application Priority Data

Aug. 21, 1974  Japan.............................. 49-96342

[52] U.S. Cl.............................. 356/73; 356/203; 356/209
[51] Int. Cl.² .................. G01N 21/22; G01N 21/48
[58] Field of Search ................ 356/73, 77, 96, 201, 356/202, 203, 209; 250/578

[56] References Cited
UNITED STATES PATENTS

| | | | |
|---|---|---|---|
| 3,096,137 | 7/1963 | Silard................... | 356/201 |
| 3,694,092 | 9/1972 | Hashimoto et al.................. | 356/201 |
| 3,746,869 | 7/1973 | Lindstedt............................ | 356/73 |
| 3,762,817 | 10/1973 | Harklav .............................. | 356/209 |
| 3,892,484 | 7/1975 | Tsuboshima et al.................. | 356/96 |

OTHER PUBLICATIONS

Verheyen et al., "Construction & Application of a Simple XY Scanning Isodensitometer", Jr. Phys. E. Sci. Instruments, vol. 4, (6–1971) pp. 435–437.

Primary Examiner—John K. Corbin
Assistant Examiner—Wm. H. Punter
Attorney, Agent, or Firm—Fidelman, Wolffe & Waldron

[57] ABSTRACT

Densitometer for quantitative determination of the content of a sample spot on a TLC plate or the like, wherein dualwavelength zigzag scanning is conducted on the spot. Light reflected and transmitted by the sample is received by photometers, and compensation based on Kubelka-Munk's theoretical equations is made on the photometer output so that the output is substantially proportional to the quantity of the substance in the spot being scanned.

19 Claims, 19 Drawing Figures

DENSITOMETER

This invention relates to improvements in densitometry and more particularly to a densitometer which enables accurate direct quantitative determination of spots of substances developed on a support used in thin-layer chromatography (TLC), paper chromatography and electrophoresis, with a high degree of accuracy and precision and good reproducibility and without being affected by various conditions such as the size and shape of the spots, as well as uneven distribution of the concentration thereof, the thickness and grain size of the thin layer and the method of development of the sample.

For direct quantitative determination of spots developed and separated on a TLC plate conventional densitometers rely on the absorption characteristics of the separated substances themselves or that of the coloring agent with which the spots are dyed. However, such conventional densitometers are designed for measurement of substances separated on a relatively transparent electrophoretic support such as acrylamide or agar gel, or cellulose acetate film, or on a sheet of filter paper in chromatography, and they cannot attain good reproducibility in direct quantitative determination of spots developed on a TLC plate.

In measurement of electrophoretic samples developed on relatively transparent supports or media such as agar gel or cellulose acetate film, substances contained in the fractions can be quantitatively determined with a fairly high degree of accuracy and precision by scanning the sample with a monochromatic light beam to obtain a pattern of the absorbance change of the sample and then by meaureing each peak area of the pattern.

In the case of TLC, however, the supporting medium is a thin layer of alumina or silica gel coating a glass plate, which scatters light, so that the absorbance values measured by a densitometer, whether it be reflected or transmitted light, are not proportional to the concentration of the substance being measured as in the case of transparent media but are so complicated as to render difficult quantitative determination of the substance. Moreover, the shape, thickness and size of the spot developed on a thin-layer plate and the distribution of the concentration of the sample component in the spot are not always uniform, and the measured values are influenced by various conditions during and after development such as the thickness and grain size of the thin layer, the manner of development, the drying time of the plate and the manner of spraying coloring agents, so that with conventional densitometers it is very difficult to perform quantitative determination of substances with a necessary and sufficient degree of accuracy and precision for daily analysis.

In most laboratories, therefore, the TLC spots are not determined by densitometry but by other analytical methods such as spectrophotometry and gas chromatography, both of which require troublesome spot scraping, extraction and dissolving procedures.

Accordingly, the primary object of the invention is to provide a densitometer which is capable of directly quantitatively determining the substance contained in TLC spots with a high degree of accuracy and precision and good reproducibility and without being affected by various measuring conditions.

In order to achieve the above object, first the apparatus of the invention employs a method of scanning a TLC spot by a thin light beam in a zigzag way. The zigzag scanning enables elimination of adverse influences on the result of measurement caused by various conditions such as the shape, size and thickness of the spot or uneven distribution of the concentration of the separated sample component in the spot. Secondly, the apparatus of the invention is provided with a function generator connected to the output of an absorbence signal producing circuit for compensating the absorbance signal so that the signal becomes proportional to the true absorbance of the separated sample component in a TLC spot under measurement. First the relation between the quantity in each unit area of the TLC spot of the substance to be measured, and the absorbance of light energy by the substance is derived from Kubelka-Munk's theoretical equations, and the characteristics of the function generator are so determined that the relation becomes linear. Integration of the output from the function generator for each TLC spot will result in accurate and precise quantitative determination of the sample component in the spot.

The invention will become apparent from the following description of a preferred embodiment thereof with reference to the accompanying drawings, wherein:

FIGS. 4(a), (b) and (c) show the principle of operation of the apparatus of the invention;

Figures 1, 1A:
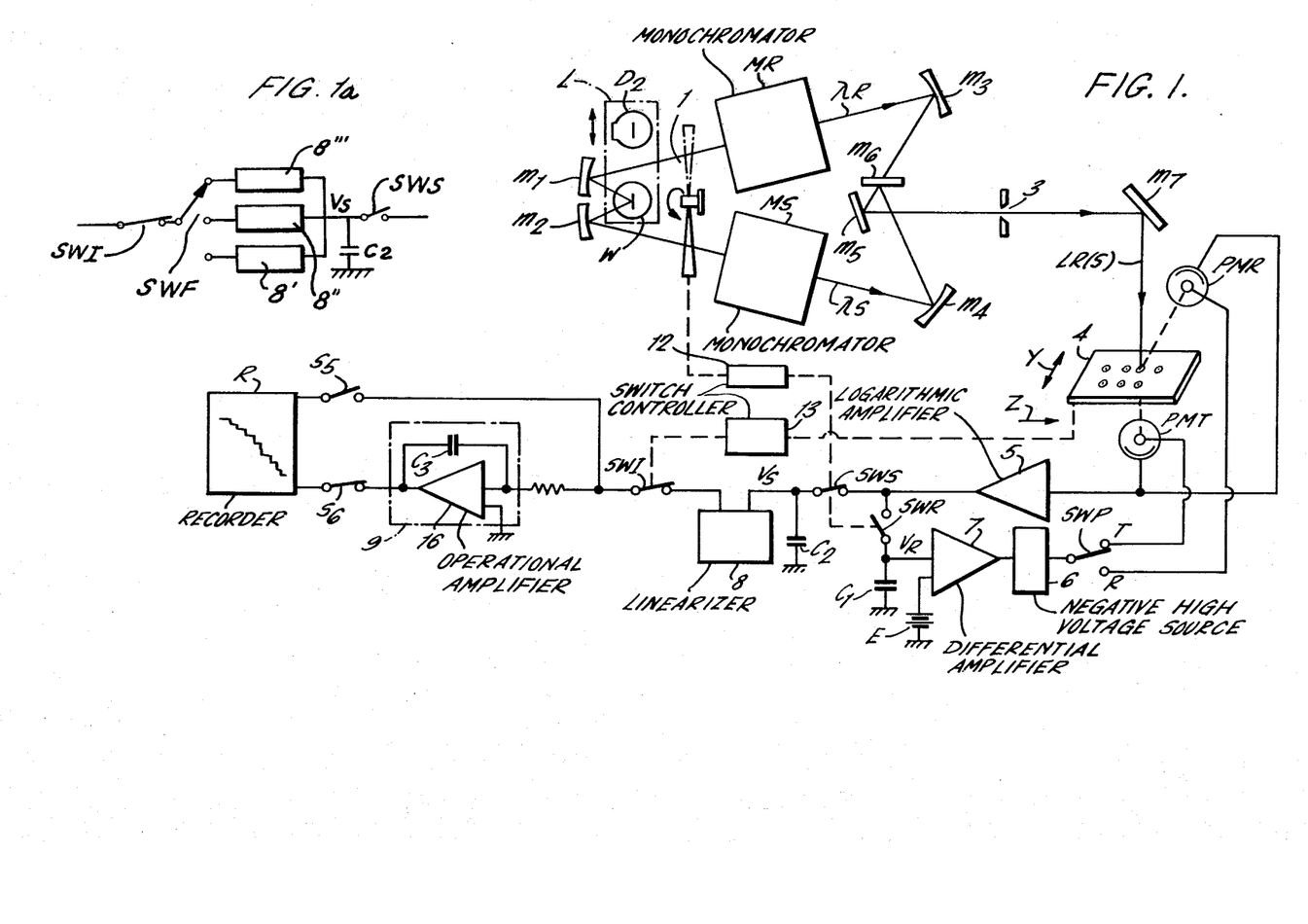
FIG. 1 shows a schematic layout of the apparatus of the invention.
FIG. 1(a) is an alternative embodiment of the linearizer of FIG. 1.

Now referring in detail to the drawings, first to FIG. 1, there is shown a source of light L comprising a tungsten lamp D. A suitable switching device not shown in provided to effect selective use of either one of the lamps for the visible or the ultraviolet region. The light from the source L is reflected by two collimating mirrors m1 and m2 so as to be introduced into two monochromators MR and MS, with a rotating chopper 1 alternately intercepting the light entering the monochromators.

The monochromators produce two monochromatic light beams of different wavelengths $\lambda R$ and $\lambda S$, respectively, which are reflected by concave mirrors m3 and m4, and caused by a half-mirror m6 to alternately impinge on a plain mirror m5 to be passed through a slit 3 and directed by a plain mirror m7 onto a TLC plate 4 perpendicularly thereto.

The plate is moved at a predetermined constant speed relative to the beam linearly in the direction Z longitudinal of the plate, that is, in the direction of development of the sample components. Simultaneously with this movement the plate is linearly reciprocally moved at a constant speed horizontally in the direction Y perpendicular to the above-mentioned direction of movement. It will be easily understood that as the plate is moved in the above manner, it is scanned by the light beam in a zigzag way. The relative zigzag movement between the beam and the plate may be effected otherwise, for example, by reciprocating the light beam along the Y-axis while moving the plate linearly along the Z-axis. A device for effecting the relative movement of the plate to the scanning beam will be described later with reference to FIG. 3.

A photodetector PMT such as a photomultiplier tube detects the light transmitted through the plate 4, while another photodetector PMR detects the light reflected by the plate 4. The output terminals of the photomultiplier tubes are connected to the input of a logarithmic amplifier 5, the output of which is connected to a signal separating device such as a pair of switches SWS and SWR for taking out the outputs from the amplifier 5 caused by the sample and reference beams λS and λR, respectively. To this end, the switches SWS and SWR are ganged with the chopper 1 through a suitable controller 12 so that when the chopper passes the light from the source to enter the monochromator MR while blocking it from the other monochromator MS, the switch SWR is closed and the switch SWS is opened, while when the chopper allows the light from the source to enter the monochromator MS while blocking it from the monochromator MR, the switch SWS is closed and the switch SWR is opened.

A capacitor C1 stores the reference beam signal VR when the switch SWR is closed, and a capacitor C2 stores the sample beam signal VS when the switch SWS is closed. The signal VR is also applied to a differential amplfier 7, to which a voltage source E provides a reference voltage. The output of the amplifier 7 controlls a negative high voltage source 6 in such a manner that the difference input (VR - E) to the amplifier 7 becomes zero.

A switch SWP is provided to selectively actuate one of the photomultiplier tubes PMT and PMR. When the movable arm of the switch SWP is brought into contact with a terminal T, the photomultiplier tube PMT is energized to detect the light transmitted through the TLC plate 4, while when the arm is switched over to a terminal R, the photomultiplier tube PMR is energized to detect the light reflected by the plate.

A function generator or linearizer 8 is connected through the switch SWS to the output of the logarithmic amplifier 5 so as to effect compensation based on Kubelka-Munk's theoretical equations as will be described later in detail. In an alternative embodiment of this invention (see FIG. 1a) a plurality of function generators 8', 8'', 8''' of different characteristics may be connected in parallel so that any desired one of them may selectively be used by means of a selection switch SWF. The detailed arrangements of the dcircuit 8 will be described later with reference to FIG. 2.

A gate switch SWI is operated in a ganged relation to the lateral reciprocal movement of the TLC plate 4 so that within a predetermined range of the lateral reciprocation of the plate 4 the switch SWI is closed to transmit the output from the circuit 8 to a signal reading device R such as a recorder, indicator or printer directly or indirectly through an integrator 9.

Suppose that there are a plurality of spots developed on the plate side by side along the direction of lateral reciprocation or swinging of the light beam relative to the plate. The operation of the switch SWI is so controlled by a suitable controller 13 that it is closed to pass the output from the circuit 8 caused by a desired one of the spots. The integrator 9 includes an operational amplfier 16 and an impedance C3 for integration.

The recorder or indicator R records or indicates the absorbance of the substance in each spot developed on the plate 4 and alternatively or simultaneously the integration output of from the integrator 9 corresponding to the sum of the absorbance of the spot.

Figure 2:
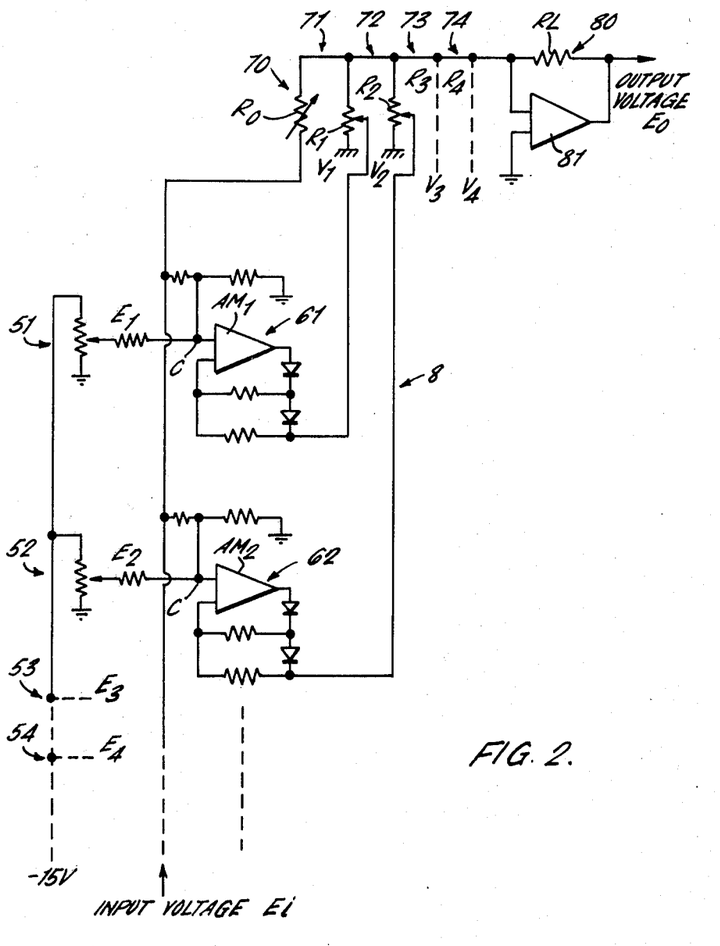
FIG. 2 shows one example of a function generator used in the apparatus shown in FIG. 1.
Figure 6A:
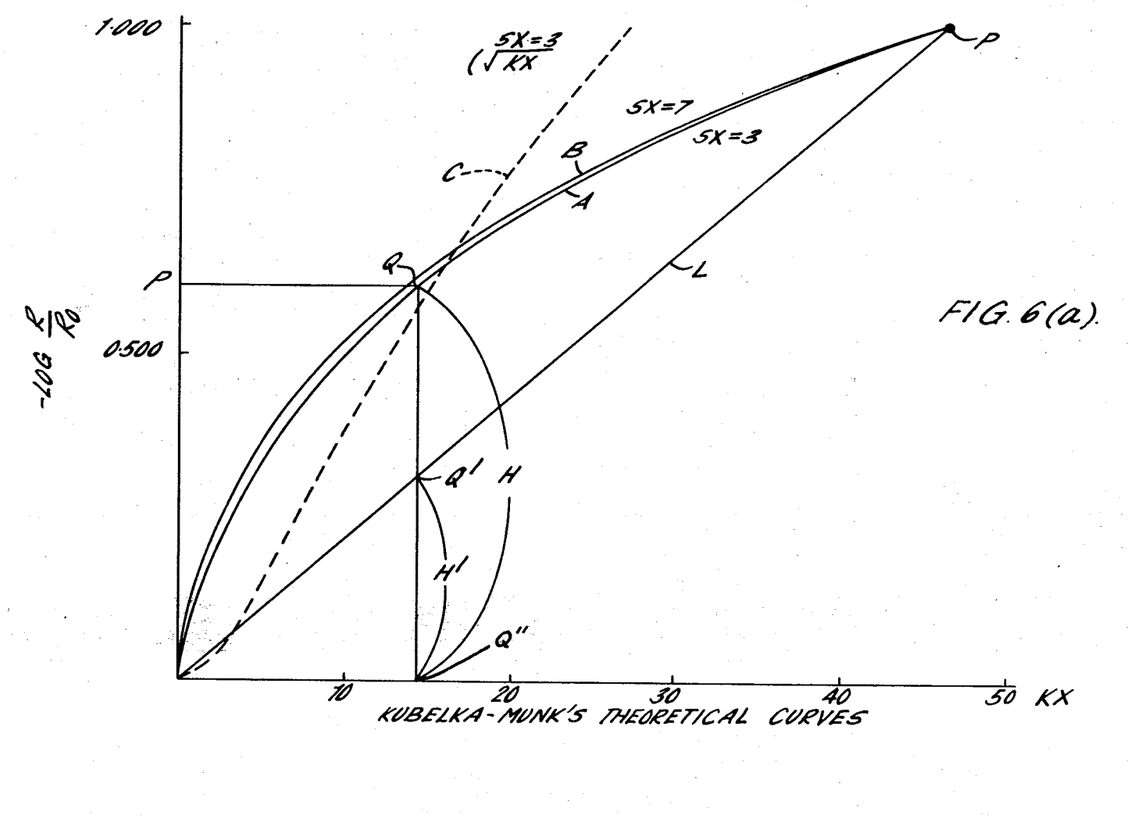
FIGS. 6(a) and 7 are graphs for explanation of the principle of compensation based on Kubelka-Munk's theoretical equations.

FIG. 2 shows in detail one example of the previously mentioned function generator 8 for carrying out compensation based on Kubelka-Munk's theoretical equations. As will be described later in detail, in accordance with Kubelka-Munk's theoretical equations the relation between the quantity (KX) per unit area of a substance to be measured and the absorbance or the reflection absorbance ($-\log R/R_o$) thereof is not linear as shown in FIG. 6(a), wherein two real-line curves A and B are plotted for different values of the scattering parameter SX, that is, SX = 3 and SX = 7, respectively. This means that the output of the logarithmic amplifier 5 is not proportional to the quantity of the substance in that area of the spot which the scanning beam hits.

Figure 7:
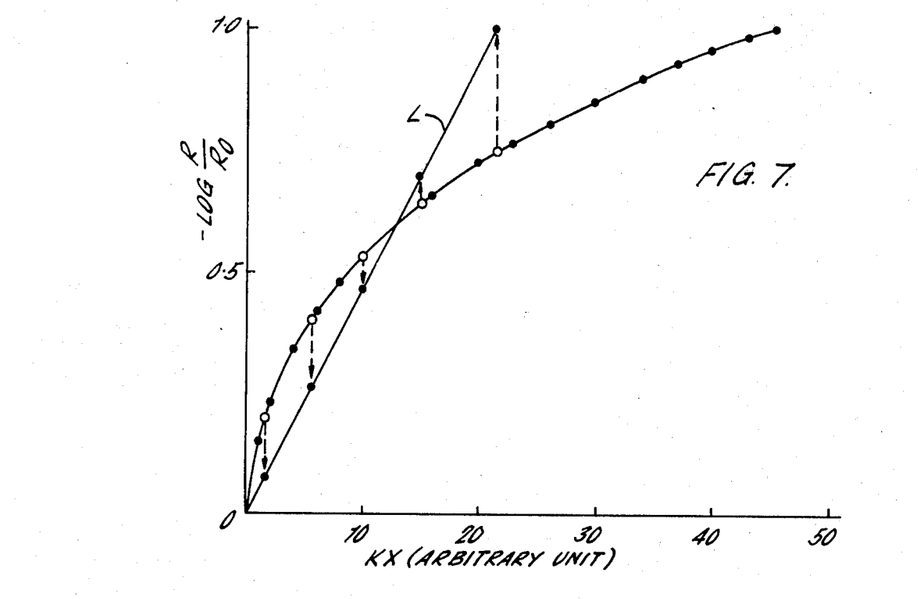

One way to render the above relation linear or proportional is to draw an arbitrary straight line L passing the origin of the coordinate axes of the graph and compensate the output of the logarithmic amplifier (which corresponds to the absorbance or reflection absorbance of the substance contained in the spot) in such a manner that several points are selected on the Y-axis and the corresponding points on the curve coincide with the line L. For example, in FIG. 6(a) a point P is selected on the Y-axis and a line from P is drawn in parallel with the X-axis, whereupon a point Q is obtained at the point of intersection of the line with, say, the curve A. Then a line is drawn from the point Q perpendicularly to the X-axis to obtain points Q' and Q'' on the straight line L and the X-axis, respectively. If the Y-values or ordinates of the points Q and Q' are H and H', respectively, H'/H is the compensation coefficient by which the output from the logarithmic amplifier 5 is to be multiplied. It will be easily seen that the compensation coefficient varies as the output of the amplifier 5 (that is, the position of P along the Y-axis) varies. The straight line may be drawn in any other way than in FIG. 6(a), such as, for example, shown in FIG. 7.

Another way to render the above-mentioned relation linear or proportional is to provide a function generator of such a characteristic that when the input which corresponds to any absorbance or reflection absorbance value on the Y-axis is FIG. 6(a) is applied to the function generator, it produces an output corresponding to the value on the X-axis of that point on the curve which corresponds to the abovementioned value on the Y- axis. FIG. 2 shows an example of such a function generator, which provides "bent line" approximations.

Figure 6B:
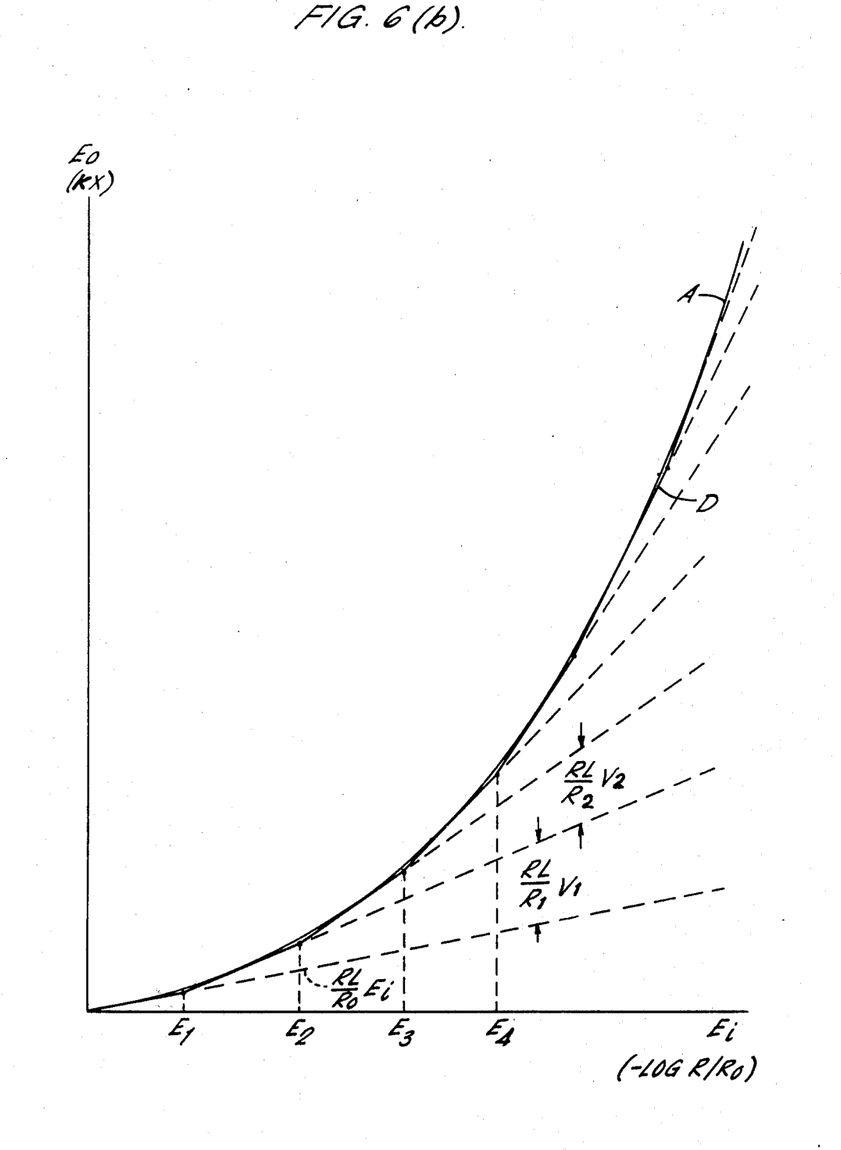
FIG. 6(b) is a graph for explanation of the principle of operation of the function generator shown in FIG. 2.

FIG. 6(b) shows one of the curves A and B in FIG. 6(a), say, the curve A plotted with KX taken along the Y-axis and the reflection absorbance (—log R/Ro) taken along the X-axis. It is this curve that is to be approximated by a bent line D obtained by the function generator of FIG. 2.

The generator comprises a plurality of variable voltage sources 51, 52, 53, 54 ..., which are so set as to produce output voltage E1, E2, E3, E4 ..., respectively, which define the bent points of the bent line D of approximation. The function generator further comprises voltage producing circuits 61, 62, ..., which comprise an operational amplifier AM1, AM2, ..., with diodes and resistors connected in the feedback circuit thereof. These circuits 61, 62, ... are of the same characteristic and are so designed that when the voltage at a point $c$ determined by both the input Ei (that is, the output of the logarithmic amplifier 5) and the corresponding one of the voltages E1, E2, E3 ... En is positive, the circuits are actuated to produce output voltages V1, V2, V3 ... Vn as expressed by the following equations wherein $a$ is a constant:

$$V1 = a\ (Ei - |E1|) \text{ when } Ei > E1,$$

$$V2 = a\ (Ei - |E2|) \text{ when } Ei > E2,$$

$$V3 = a\ (Ei - |E3|) \text{ when } Ei > E3,$$

.
.
.

$$Vn = a\ (Ei - |En|) \text{ when } Ei > En.$$

The function generator further comprises variable current sources 70, 71, 72 ... which comprise variable resistors Ro, R1, R2, ..., Rn, respectively, and generate currents proportional to the voltages Ei, V1, V2 ... Vn, respectively; and an adder 80 consisting of an operational amplifier 81 and a resistor RL. The output Eo of the circuit will then be given by the following equation:

$$Eo = Ei/Ro + V1/R1 + V2/R2 \ldots + Vn/Rn)RL$$

The setting of the above function generator is based on Kubelka-Munk's theoretical curves. With the input voltage Ei being suplied by the output from the logarithmic amplifier 5 which corresponds to the absorbance or the reflection absorbance of the sample being measured, the voltage levels E1, E2 ... are suitably set and the resistors R1, R2 ... Rn are so adjusted successively in the order mentioned that the bent line D expressing the output Eo substantially coincides with the curve A. The principle and operation of the circuit of FIG. 2 will be clearly understood by reference to FIG. 6(b).

Figure 3:
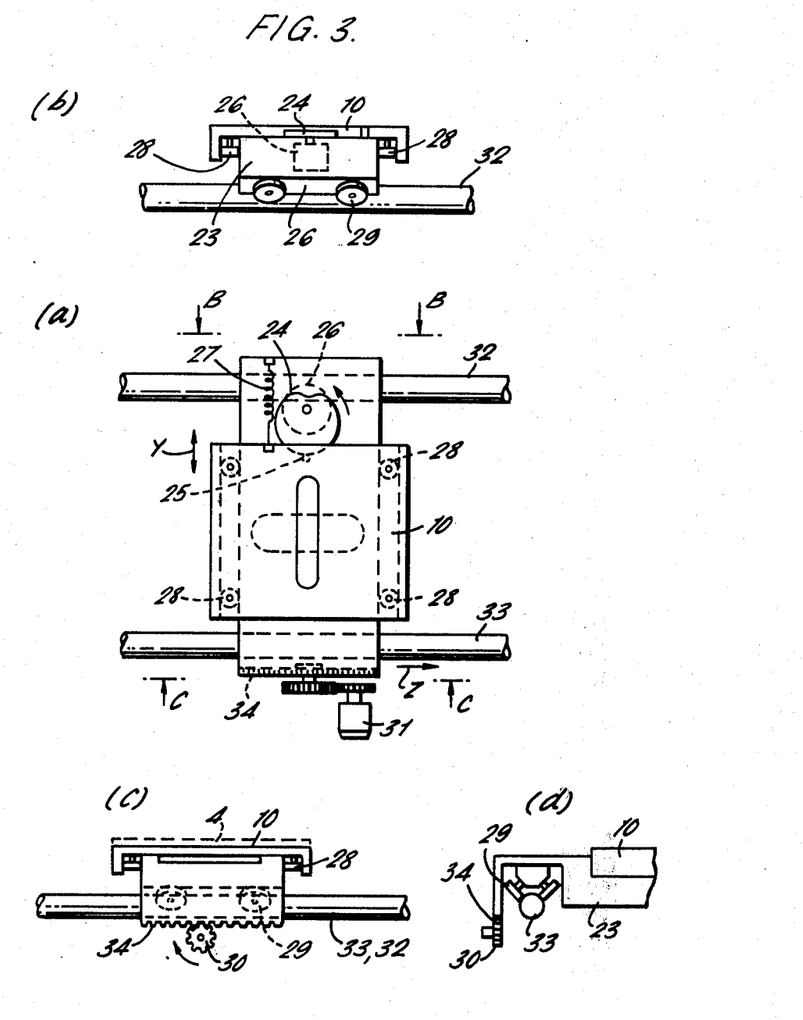
FIG. 3(a) is a top plan view of a mechanism for effecting the zigzag movement of a TLC plate relative to the scanning light beam.
FIG. 3(b) is an elevational view as viewed in the direction of arrows B in FIG. 3(a)
FIG. 3(c) is an elevational view as viewed in the direction of arrows C in FIG. 3(a)
FIG. 3(d) is a right hand side view of FIG. 3(c)

FIG. 3 shows by way of example a mechanism for effecting the zigzag movement of the plate 4 relative to the scanning beam LR or LS. The plate 4 is placed on a support 10, which is in turn mounted on a carriage 23 so as to be slidable relative thereto by means of rollers 28 in the direction of an arrow Y. To this end, an eccentric cam 24 fixed to the output shaft of a motor 26 mounted on the carriage 23 bears against a cam follower 25 attached to the support, with a spring 27 having its opposite ends fixed to the support 10 and the carriage 23 thereby biasing the support toward the cam. As the motor 26 rotates the cam 24, the support 10 is moved in the Y-direction on the carriage 23 by or against the force of the spring 27.

On the other hand, the carriage 23 is carried on a pair of guide rails 32 and 33 through the intermediary of rollers 29 and has at one side thereof a rack 34 which is engaged by a pinion 30 meshing with the output gear of a motor 31 secured to a machine frame, not shown. As the motor 31 rotates, the carriage 23 is moved on the rails 32 and 33 in the direction of an arrow Z. Combination of the movements in the Y- and Z-directions will result in a zigzag movement of the plate 4 relative to the beam LR(S) as shown in FIG. 4(a).

Now the operation of the system will be explained. The light signals having wavelengths λS and λR are alternately directed onto the TLC plate 4. The light transmitted through the sample spot on the plate enters the photomultiplier tubes PMT while the light reflected by the plate 4 is received by the other photomultiplier tube PMR. The two photomultiplier tubes are selectively actuated by the switch SWP to convert the light signals to corresponding electrical signals. These signals corresponding to the light signals λS and λR are amplified and converted by the logarithmic amplifier 5 to a signal corresponding to the absorbance or reflection absorbance of the sample being measured.

The gate switches SWS and SWR are operated by the switch controller 12 in ganged relation to the rotating chopper 1 so that when the reference light beam having the wavelength of λR is detected, the switch SWR is closed, with the switch SWS being opened, so that the differential amplifier 7 automatically controls the gain of the photomultiplier tube PMR or PMT thereby to keep the output from the logarithmic amplifier 5 caused by the reference beam λR at the same constant level as E. On the other hand, when the sample beam signal having the wavelength of λS is detected, the switch SWR is opened and the switch SWS is closed so that the output from the amplifier 5 is applied to the compensating circuit 8, the output of which is accurately proportional to the quantity of the sample component in that area of the spot on which the scanning beam LS is incident. The output of the circuit 8 is then recorded in the recorder R either directly or through the integrator 9.

Figure 4:
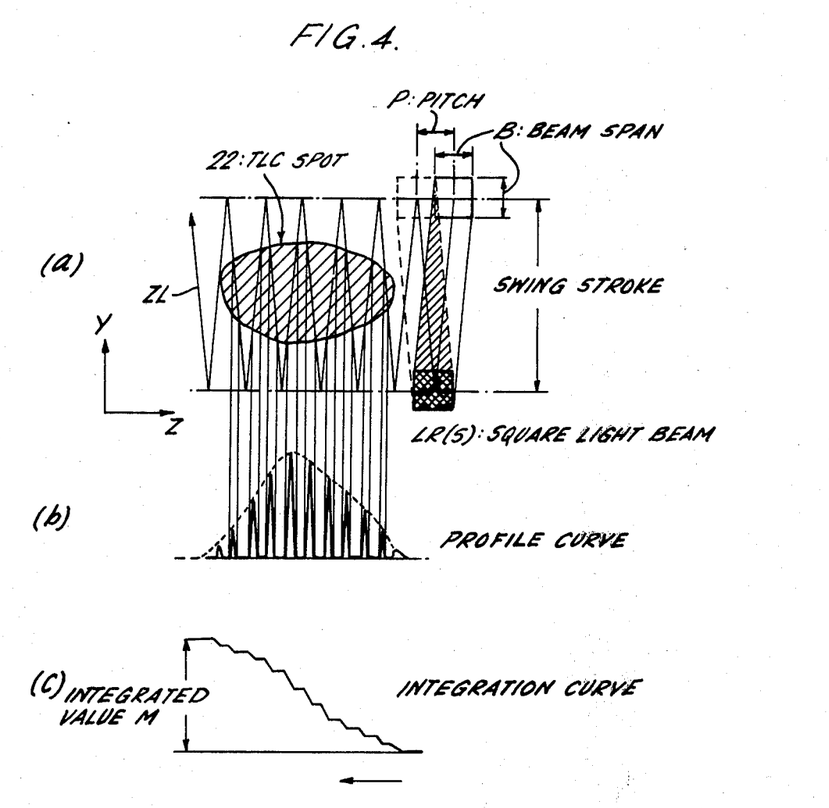

When the switch S5 is closed, with the switch S6 being opened, the chart in the recorder is fed in synchronism with the zigzag scanning movement of the TLC plate 4, so that a profile curve as shown in FIG. 4(b) is drawn on the chart for each spot. When the switch S6 is closed with the switch S5 being opened, the output signal from the compensator 8 shown as a series of spike-like peaks in FIG. 4(b) is integrated and recorded on the chart of the recorder R as a stepped integration curve shown in FIG. 4(c). The value or height M from the baseline where the integration curve becomes flat indicates the total quantity of the sample component in the spot that has been scanned.

As the TLC plate 4 is moved in a horizontal plane linearly in the Z-direction at a constant speed and at the same time linearly reciprocally in the Y-direction at another constant speed, the beam LR(S) scans a TLC spot 22 on the plate in a zigzag locus ZL as shown enlarged in FIG. 4(a). The scanning beam LR(S) preferably has a minute square cross-sectional area less than one-tenth of the area of the spot to be scanned. If the speeds of the movements of the plate in the Z- and Y-directions are so selected that the pitch P of the zig-zag scanning locus is equal to the length B of one side of the square cross section of the scanning beam, that is, if the plate is moved a distance of ½B in the Z-direction during one swing stroke thereof, it follows that the whole area of the spot is scanned twice by the beam.

The advantages of the dual-wavelength zigzag scanning system of the invention will now be described on the assumption that Lambert-Beer's law for measurement of a solution applies to the present case although strictly the law does not apply to the TLC plate due to scattering by the plate itself. That is, it is assumed that the thin layer of the TLC plate corresponds to the solvent and the spot corresponds to the sample to be measured in the case of measuring solution, and that the spot is optically uniform in the direction of the thickness thereof.

Figure 5A:
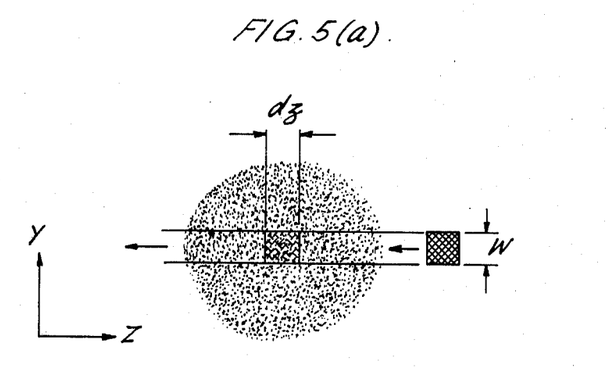
FIGS. 5(a) and 5(b) show two conventional methods of linear scanning.

Suppose that a spot developed on a TLC plate is scanned with a light beam of a single wavelength in only one direction, for example, in the Z-direction as shown in FIG. 5(a). If the intensity of the incident light is Io and that of the transmitted light is I, the transmittance T is given by I/Io. The relation between I and Io is also expressed as:

$$I = I_0 \cdot e^{-acx} \tag{1}$$

where $a$ is the molecular absorption coefficient that the substance of the spot has for a given wavelength; $c$ is the concentration of the substance; and $x$ is the thickness of TLC plate.

Since the absorbance A is given by $A = \log(I_0/I) = acx$, the substance contained in the spot can be quantitatively determined by integrating the peak area of the absorbance curve. If the quantity of the substance is M, $$M = \int cxw \, dz \tag{2}$$

where $w$ is the width of the beam.

Applying the equation (1) to the equation (2), we obtain $$M = \frac{w}{a} \int \log \frac{I_0}{I} \, dz = \frac{w}{a} \int \log \frac{1}{T} \, dz \tag{3}$$

The quantity M of the substance obtained, however, is that contained in that elongated thin area of the spot which extends along the scanning direction of the beam and has a width corresponding to that $w$ of the beam and is not the quantity of the whole substance contained in the spot. For example, if the center of distribution of the separated substance is displaced from the scanning line, or if the spot is laterally spread or diffused, the above single-wavelength unidirectional scanning cannot provide an accurate quantitative determination of the substance contained in the spot.

Figure 5B:
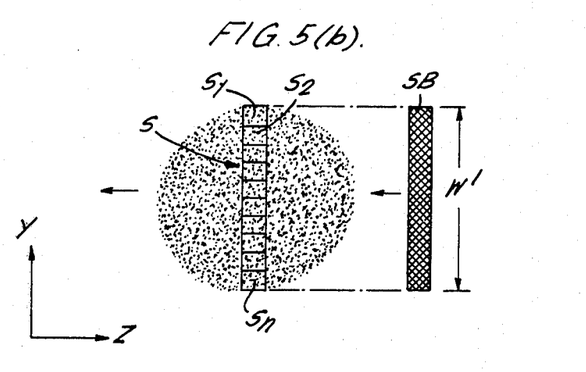

In order to eliminate the above defect of the unidirectional scanning by a beam having a small width, a slim beam SB having the same width $w'$ as the diameter of the spot to be scanned may be used, as shown in FIG. 5(b). However, the such a slim beam it is not possible to measure the correct quantity of the spot. Suppose that that area S of the spot which the slim light beam hits is divided into equal minute sections S1, S2 ... Sn having the same area; that the quantities contained in the sections S1, S2 ... Sn are m1, m2 ... $m_n$, respectively; and that the intensities of the incident light on the sections are Io1, Io2 ... $Io_n$ and the intensities of the light transmitted through the sections are I1, I2 ... In, respectively. The quantity M of the substance contained in the area S is given by $$M = m_1 + m_2 + m_n$$

$$= \frac{S}{a} \left( \log \frac{I_{o_1}}{I_1} + \log \frac{I_{o_2}}{I_2} + \ldots + \log \frac{I_{o_n}}{I_n} \right)$$

$$= \frac{S}{a} \log \frac{I_{o_1} \cdot I_{o_2} \ldots I_{o_n}}{I_1 \cdot I_2 \ldots I_n} \tag{4}$$

However, the quantity M' of the area S measured by the slim beam SB is given by:

$$M' = \frac{S}{a} \log \frac{I_{o_1} + I_{o_2} + \ldots + I_{o_n}}{I_1 + I_2 + \ldots + I_n} \tag{5}$$

As is obvious, the equations (4) and (5) are different. In other words, with the slim beam it is impossible to correctly measure the quantity of the substance in the spot.

On the contrary, the zigzag scanning method of the invention as shown in FIG. 4(a) produces a profile curve as shown in FIG. 4(b). The area of each of the peaks is expressed as:

$$\frac{B}{a} \int \log \frac{1}{T} \, dy \tag{6}$$

This integral value expresses the total quantity of the substance contained in that area of the spot which is covered by the beam having a width B in the Z-direction when the beam scans the spot one way in the Y-direction. Therefore, integration along the Z-axis with a sufficiently small value of B will yield $$\frac{1}{a} \iint_{\text{Spot}} \log \frac{1}{t} \, dy \, dz \tag{7}$$

which accurately expresses the quantity of the whole substance contained in the spot. The value can be obtained only by the zigzag scanning method of the invention.

The advantage that can be attained by the dual-wavelength scanning of the invention is that if the beams of the two wavelengths are passed along one and the same path through the sample, baseline noises resulting from other causes than the sample component to be measured, such as apparent absorption due to unevenness in the thickness of the thin layer or minute scars therein, are common with the light beams of the two wavelengths, so that they can be compensated for by comparing the values measured with the light beams of the two wavelengths.

Now the compensation based on Kubelka-Munk's theoretical equations will be explained. Kubelka-Munk's theoretical equations are expressed as follows:

$$-\frac{di}{dx} = -(S + K)i + Sj$$

$$\frac{dj}{dx} = -(S + K)j + Si$$

where $i$ is the intensity of light advancing within the thin layer toward the surface thereof on which light is not incident; $j$ is the intensity of light advancing within the thin layer toward the surface thereof on which light is incident; $S$ is the scattering coefficient per unit thickness of the thin layer; $K$ is absorption coefficient per unit thickness of the thin layer; and $x$ is the thickness of the thin layer from the surface thereof on which light is not incident.

Solving the above equations for $i$ and $j$ yields $$i = A \sinh(bSx) + B \cosh(bSx)$$

$$j = (aA - bB) \sinh(bSx) + (aB - bA) \cosh(bSx)$$

where $$a = \frac{S+K}{S}, \quad b = \sqrt{a^2 - 1},$$

and A and B are constants.

The boundary conditions are as follows: If $x = 0$, $i = IoT$ and $j = 0$; and if $x = X$, $i = Io$ and $j = IoR$. Therefore, the transmittance T and the reflectance R are expressed as:

$$T = \frac{b}{a \sinh(bSX) + b \cosh(bSX)}, \text{ and}$$

$$R = \frac{\sinh(bSX)}{a \sinh(bSX) + b \cosh(bSX)} \tag{8}$$

wherein $X$ is the thickness of the thin layer; and $Io$ is the intensity of the incident light.

If the thin layer absorbs no light, that is, if $K = 0$, the transmittance T and the reflectance R will become $$T = To = \frac{1}{SX+1}, \text{ and } R = Ro = \frac{SX}{SX+1} \tag{9}$$

If $a$ and $b$ are expressed by SX and KX, we obtain $$a = \frac{S+K}{S} = \frac{SX+KX}{SX}, \text{ and}$$

$$b = \sqrt{a^2-1} = \frac{\sqrt{KX(2SX+KX)}}{SX}$$

Using the reflectances R and Ro obtained from the equations (8) and (9), the relation between the reflection absorbance, that is, $-\log R/Ro$ and the absorption factor KX have been calculated for the scattering parameter $SX = 3$ and $SX = 7$, and the results of the calculation are plotted as real-line curves A and B in FIG. 6(a).

The broken-line curve C in FIG. 6(a) is plotted for $SX = 3$, with $\sqrt{KX}$ being taken along the X-axis. As shown in FIG. 6(a), Kubelka-Munk's theoretical equations express somewhat complicated curves.

Various conditions for application of these theoretical curves to thin-layer densitometry will be considered below. If the thickness X of the thin layer is uniform, the absorption coefficient K corresponds to the quantity of the sample component per unit area and unit thickness of the spot. Therefore, the absorption factor KX can be considered to correspond to the quantity of the sample component contained in the whole thickness of the thin layer within a unit area of the TLC spot being scanned. In this case, the distribution of the sample component must be uniform within the incident light beam. On the other hand, in conventional densitometers the scanning light beam defined by a slit has a relatively large cross section, within which the distribution of the sample component is not uniform. Therefore, it is impossible to compensate the absorbance obtained, using the graph of FIG. 6(a). The light beam used for the zigzag scanning of this invention has a minute cross section as small as 1.25 mm × 1.25 mm.

In order to determine whether it is possible to consider the distribution of the substance in a TLC spot as being uniform within the cross-sectional area of the above-mentioned scanning beam of the invention used for actual measurement, a circular spot of a high concentration substance having a diameter of 7 mm has been scanned for quantitative determination by a beam the cross section of which has a width of 1.25 mm and a length varying within a range of 0.5 mm to 7 mm. The integrated value, that is, the output from the integrator 9 of the system of FIG. 1 has been found constant when the length is less than 2 mm. This means that a beam having a cross section of 1.25 mm × 1.25 mm is sufficient for the purpose.

Using the densitometer of the invention the following experiments were conducted.

EXPERIMENT 1

Caffeine was developed on a slica gel thin-layer plate produced by Merck & Co., Inc., New Jersey, U.S.A., and the separated spots were scanned by the densitometer of the invention with the reference and sample beams having wavelengths of 350 nm and 270 nm, respectively, for plotting calibration curves. The value SX was set to 3 in this and also the following EXPERIMENTS 2 to 4. The results of measurement were plotted in FIG. 8, wherein the quantity of caffeine is taken along the X-axis and the output of the integrator 9 along the Y-axis.

Figure 8:
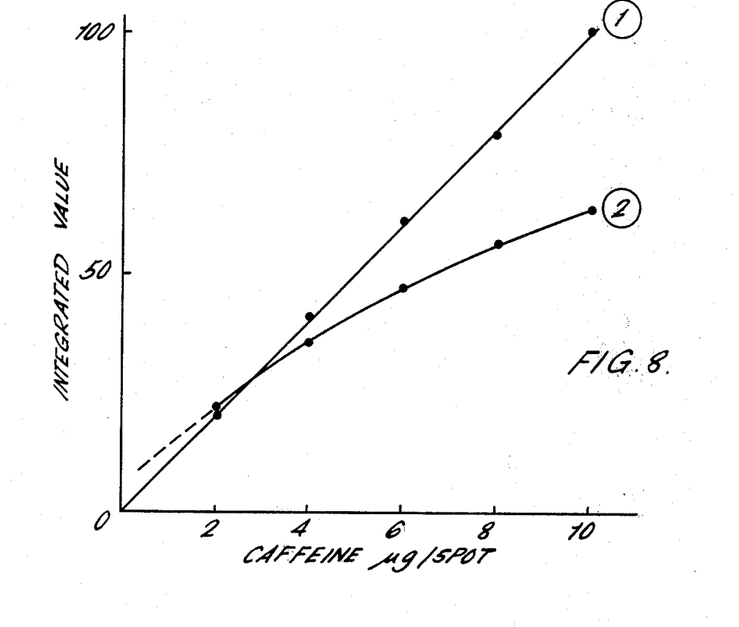
FIGS. 8 and 9 are graphs showing the results of measurement obtained by the apparatus of the invention and those obtained by a conventional apparatus.

The curve (2) was obtained when the compensating circuit 8 in FIG. 1 was not used, while the straight line (1) passing the origin was obtained when the circuit 8 was connected.

EXPERIMENT 2

Figure 10:
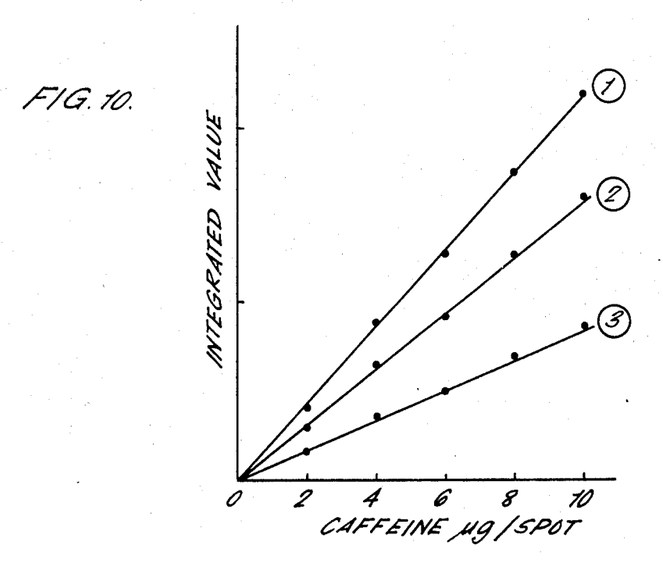
FIGS. 10 and 11 are graphs showing the results of measurement obtained by the apparatus of the invention.

Measurement was conducted on the same thin-layer plate as in EXPERIMENT 1 but with the sample beam λS of different wavelengths. The results are shown in FIG. 10. As clearly shown, even when the wavelength of the sample beam was changed from 276 nm where absorption is the strongest to 282 nm and further to 286 nm where it is the weakest, the resultant straight lines (1), (2) and (3) all pass the origin although the value K corresponding to the molecular extinction coefficient varies. From this it can be concluded that Kubelka-Munk's theoretical curves very well express the relation between the reflection absorbance of the spot on the thin-layer and the concentration of the substance in the spot, and that the effects of variation of the scanning wavelength on the result of measurement are negligible.

EXPERIMENT 3

Figure 9:
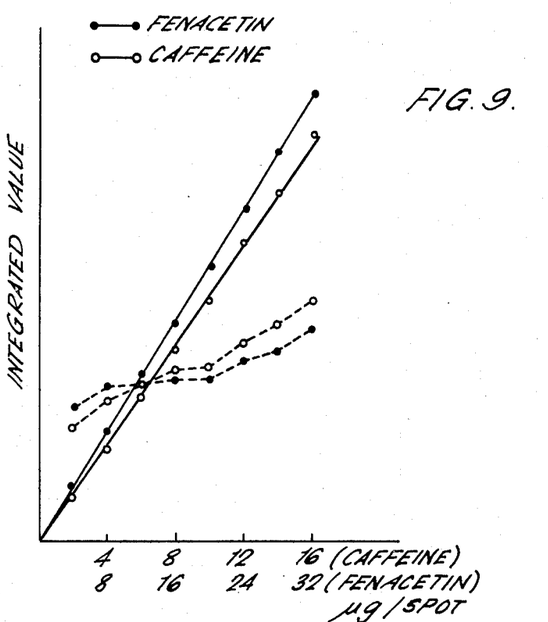

Caffeine and fenacetin were developed on the above-mentioned thin-layer plate and the results of scanning of the separated spots are plotted on the graph of FIG. 9. The broken-line curves were obtained by the conventional linear scanning with a light beam having the same width as the diameter of the spot, while the real-line straight lines were obtained by the dual-wavelength zigzag scanning of the invention.

EXPERIMENT 4

Figure 11:
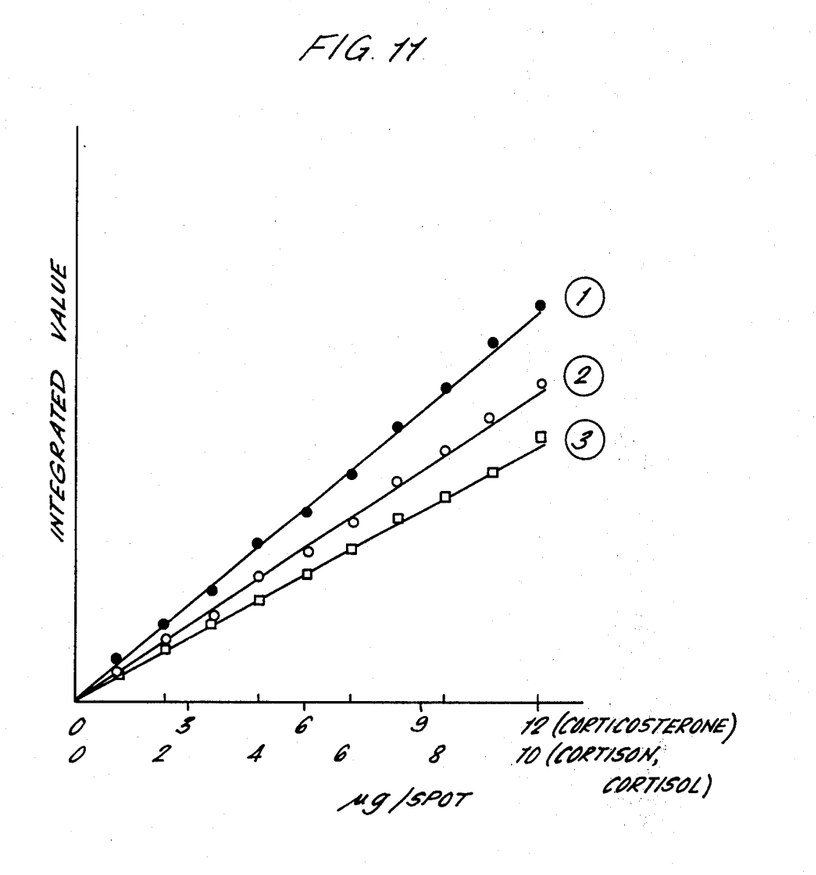

FIG. 11 shows the results of measurement of corticosterone (1), cortison (2) and coretisol (3) developed on the same plate as in EXPERIMENT 2. The same wavelength λS as in EXPERIMENT 2 was used. The graph clearly shows that the same value of SX can be applied to different measuring wavelengths or different samples to be measured.

EXPERIMENT 5

With a silica gel plate FM manufactured by Wako Junyaku Co. Ltd., Osaka, Japan, a good result was obtained with SX = 7.

What we claim is:

1. A densitometer comprising: means for providing monochromatic light; means for supporting a sample to be measured; optical means for directing said monochromatic light to said sample; photoelectric means for receiving said monochromatic light transmitted through or reflected by said sample to produce a corresponding output electrical signal; means for effecting a relative zigzag movement between said light and said sample; and means for compensating said output signal for the nonlinearity caused by scattering of said monochromatic light projected onto said sample, said compensating means comprising a plurality of function generators which are selectively connected, wherein said function generators perform their respective compensations based on Kubelka-Munk's theoretical equations said equations being expressed as follows:

$$-\frac{di}{dx} = -(S+K)i + Sj$$

$$\frac{dj}{dx} = -(S+K)j + Si$$

where $i$ is the intensity of light advancing within the thin layer toward the surface thereof on which light is not incident; $j$ is the intensity of light advancing within the thin layer toward the surface thereof on which light is incident; $S$ is the scattering coefficient per unit thickness of the thin layer; $K$ is absorption coefficient per unit thickness of the thin layer; and $x$ is the thickness of the thin layer from the surface thereof on which light is not incident.

2. A densitometer comprising: means for providing monochromatic light; means for supporting a sample to be measured; optical means for directing said monochromatic light to said sample; photoelectric means for receiving said monochromatic light transmitted through or reflected by said sample to produce a corresponding output electrical signal; means for effecting a relative zigzag movement between said light and said sample; and a function generator for compensating said output signal for the nonlinearity caused by scattering of said monochromatic light projected onto said sample, said compensation based on Kubelka-Munk's theoretical equations, said equations being expressed as follows:

$$-\frac{di}{dx} = -(S+K)i + Sj$$

$$\frac{dj}{dx} = -(S+K)j + Si$$

where $i$ is the intensity of light advancing within the thin layer toward the surface thereof on which light is not incident; $j$ is the intensity of light advancing within the thin layer toward the surface thereof on which light is incident; $S$ is the scattering coefficient per unit thickness of the thin layer; $K$ is absorption coefficient per unit thickness of the thin layer; and $x$ is the thickness of the thin layer from the surface thereof on which light is not incident.

3. The densitometer of claim 2, wherein said momochromatic light providing means comprises a pair of monochromators each producing two monochromatic light beams of different wavelengths; and said optical means includes a chopper for causing said two light beams to be alternately produced and causes said two alternate light beams to be passed along a common path and projected on said sample perpendicularly thereto.

4. The densitometer of claim 2, wherein said sample is a spot developed on a thin-layer chromatographic plate.

5. The densitometer of claim 2, wherein said sample is a spot developed on a sheet of filter paper in paper chromatography.

6. The densitometer of claim 2, wherein said sample is a spot developed on an electrophoretic supporting medium.

7. The densitometer of claim 2, wherein said means for effecting a relative zigzag movement between said monochromatic light and said sample comprises: carriage means on which said sample supporting means is carried for relative movement thereto; first drive means for moving said sample carriage means relative to said monochromatic light at a first constant speed linearly in one direction in a plane perpendicular to the path of said monochromatic light; and second drive means operative simultaneously with said first drive means for moving said sample supporting means relative to said carriage at a second constant speed linearly and reciprocally in a plane parallel with said plane, so that said monochromatic light scans said sample along a zigzag locus.

8. The densitometer of claim 2, wherein said photoelectric means comprises a first photomultiplier tube for receiving said monochromatic light transmitted through said sample and a second photomultiplier tube for receiving said monochromatic light reflected by said sample.

9. The densitometer of claim 2, further including means for reading said compensated signal.

10. The densitometer of claim 2, further including means connected to the output of said compensating means for integrating said compensated signal.

11. The densitometer of claim 10, further including means for reading the output from said integrating means.

12. The densitometer of claim 2, further including means connected between said photoelectric means and said compensating means for converting said output signal from said photoelectric means to an absorbance or reflection absorbance signal.

13. The densitometer of claim 12, wherein said converting means comprises a logarithmic amplifier.

14. The densitometer of claim 2, wherein said means for effecting a relative zigzag movement between said light and said sample comprises means for moving said light and said sample relative to the other in one direction paralleling a first axis and at the same time moving reciprocally paralleling a second axis, said second axis being perpendicular to said first axis.

15. The densitometer of claim 14, further including control means operable in association with said moving means to pass the output of said photoelectric means only within a predetermined portion of each stroke of said reciprocating movement relative to the other of said light and said sample parallel to said second axis.

16. The densitometer of claim 15, wherein said control means is a switch and a controller therefor.

17. A densitometer comprising: means for providing monochromatic light; means for supporting a sample to be measured; optical means for directing said monochromatic light to said sample; photoelectric means for receiving said monochromatic light transmitted through or reflected by said sample to produce a corresponding output electrical signal; means for effecting a relative zigzag movement between said light and said sample comprising means for moving one of said light and said sample relative to the other in one direction paralleling a first axis and at the same time reciprocally paralleling a second axis perpendicular to said first axis, wherein said moving means moves relative to the other said light and said sample parallel to said first axis a distance equal to half the span length, measured parallel to said first axis, of the cross section of the light beam of said light during each one stroke of reciprocation relative to the other and parallel to said second axis; and means for compensating said output signal for the non-linearity caused by scattering of said monochromatic light projected onto said sample.

18. The densitometer of claim 17, wherein said compensating means comprises a function generator.

19. The densitometer of claim 17, wherein said compensating means comprises a plurality of function generators which are selectively connected to said converting means.

* * * * *